US008226414B2

(12) United States Patent
Bodin et al.

(10) Patent No.: US 8,226,414 B2
(45) Date of Patent: Jul. 24, 2012

(54) GENERATING POLICY DRIVEN MEAL PLANS

(75) Inventors: William Kress Bodin, Austin, TX (US); Michael Lee Masterson, Cedar Park, TX (US); Stephen James Watt, Leander, TX (US)

(73) Assignee: International Business Machines Corporation, Armonk, NY (US)

( * ) Notice: Subject to any disclaimer, the term of this patent is extended or adjusted under 35 U.S.C. 154(b) by 1166 days.

(21) Appl. No.: 11/467,190

(22) Filed: Aug. 25, 2006

(65) Prior Publication Data
US 2008/0052001 A1   Feb. 28, 2008

(51) Int. Cl.
*G09B 11/00* (2006.01)
(52) U.S. Cl. ............... 434/127; 128/921; 705/28
(58) Field of Classification Search ............. 434/127; 128/921; 705/26–28
See application file for complete search history.

(56) References Cited

U.S. PATENT DOCUMENTS

| 4,093,032 | A | 6/1978 | Uyama et al. |
|---|---|---|---|
| 4,563,739 | A | 1/1986 | Gerpheide et al. |
| 4,627,504 | A | 12/1986 | Moran |
| 4,964,053 | A | 10/1990 | Humble |
| 5,014,798 | A | 5/1991 | Glynn |
| 5,335,509 | A | 8/1994 | Namisniak et al. |
| 5,418,334 | A | 5/1995 | Williams |
| 5,487,276 | A | 1/1996 | Namisniak et al. |
| 5,671,362 | A | 9/1997 | Cowe et al. |
| 5,711,160 | A | 1/1998 | Namisniak et al. |
| 5,726,880 | A | 3/1998 | Bailey et al. |
| 5,920,261 | A | 7/1999 | Hughes et al. |
| 6,032,128 | A | 2/2000 | Morrison et al. |
| 6,089,498 | A | 7/2000 | Sticht |
| 6,101,826 | A | 8/2000 | Bessler |
| 6,158,381 | A | 12/2000 | Bray |
| 6,204,763 | B1 * | 3/2001 | Sone .................. 340/568.1 |
| 6,327,576 | B1 | 12/2001 | Ogasawara |

(Continued)

FOREIGN PATENT DOCUMENTS

JP          08128881 A     3/2011

(Continued)

OTHER PUBLICATIONS

Scher, "RFID Shelf Antennas Featuring Dynasys de-Q Tuning", pp. 1-7, retrieved May 30, 2006 http://rfidusa.com/superstore/product_info.php?cPath=21_39_60&products_id=223.

(Continued)

*Primary Examiner* — Kathleen Mosser
(74) *Attorney, Agent, or Firm* — Yee & Associates, P.C.; Mark C. Vallone

(57) ABSTRACT

A method and computer usable program product for generating meal plans based on a set of nutritional policies. The process determines nutritional requirements specified by a set of nutritional policies in response to receiving a request for a set of meal plans for a set of users. The set of nutritional policies correspond to the set of users. The process identifies a set of potential meal plans in response to determining the nutritional requirements specified by the set of nutritional policies. Each potential meal plan in the set of potential meal plans satisfies all nutritional requirements for the set of nutritional policies. The process generates a listing of ingredients required by the selected meal plan that is unavailable in a current inventory in an amount required by the selected meal plan, in response to receiving a selection of a potential meal plan to form a selected meal plan.

10 Claims, 7 Drawing Sheets

U.S. PATENT DOCUMENTS

| | | |
|---|---|---|
| 6,393,848 B2 | 5/2002 | Roh et al. |
| 6,453,687 B2 | 9/2002 | Sharood et al. |
| 6,481,602 B1 | 11/2002 | Fritze et al. |
| 6,519,963 B2 | 2/2003 | Maeda |
| 6,552,663 B2 | 4/2003 | Swartzel et al. |
| 6,693,539 B2 | 2/2004 | Bowers et al. |
| 6,741,236 B2 | 5/2004 | Yun |
| 6,755,031 B2 | 6/2004 | Cho et al. |
| 6,758,397 B2 | 7/2004 | Catan |
| 6,859,745 B2 | 2/2005 | Carr et al. |
| 6,892,545 B2 | 5/2005 | Ishikawa et al. |
| 6,919,795 B2 | 7/2005 | Roseen |
| 6,950,095 B2 | 9/2005 | Kim et al. |
| 6,975,910 B1 * | 12/2005 | Brown et al. .......... 700/90 |
| 6,982,640 B2 | 1/2006 | Lindsay et al. |
| 7,009,519 B2 | 3/2006 | Leonard et al. |
| 7,017,359 B2 | 3/2006 | Kim et al. |
| 7,027,958 B2 | 4/2006 | Singh et al. |
| 7,032,408 B2 | 4/2006 | Dentella et al. |
| 7,040,455 B2 | 5/2006 | Bogat |
| 7,044,370 B2 | 5/2006 | Bellis, Jr. et al. |
| 7,053,773 B2 | 5/2006 | McGarry et al. |
| 7,065,501 B1 * | 6/2006 | Brown et al. .......... 705/28 |
| 7,096,221 B2 | 8/2006 | Nakano |
| 7,158,035 B2 | 1/2007 | Sakamoto et al. |
| 7,182,259 B2 | 2/2007 | Lubow et al. |
| 7,340,414 B2 | 3/2008 | Roh et al. |
| 7,378,968 B2 | 5/2008 | Wang et al. |
| 7,382,267 B2 | 6/2008 | Brendley et al. |
| 7,495,561 B2 | 2/2009 | Bodin et al. |
| 7,518,516 B2 | 4/2009 | Azevedo et al. |
| 7,535,337 B2 | 5/2009 | Overhultz et al. |
| 7,648,065 B2 | 1/2010 | Marino |
| 7,663,497 B2 | 2/2010 | Chishima et al. |
| 7,673,464 B2 | 3/2010 | Bodin et al. |
| 7,680,691 B2 | 3/2010 | Kimball et al. |
| 7,682,830 B2 | 3/2010 | Prusik et al. |
| 7,716,935 B2 | 5/2010 | Kim et al. |
| 7,844,509 B2 | 11/2010 | Bodin et al. |
| 7,930,221 B2 | 4/2011 | Brown et al. |
| 7,961,104 B2 | 6/2011 | Bodin et al. |
| 8,055,555 B2 | 11/2011 | Todd et al. |
| 2002/0003531 A1 | 1/2002 | Kim et al. |
| 2002/0026325 A1 | 2/2002 | Hirahara et al. |
| 2002/0066279 A1 | 6/2002 | Kiyomatsu |
| 2002/0139848 A1 | 10/2002 | Catan |
| 2002/0143624 A1 | 10/2002 | Catan |
| 2002/0157411 A1 | 10/2002 | Ishikawa et al. |
| 2002/0178066 A1 | 11/2002 | Roh et al. |
| 2003/0014323 A1 * | 1/2003 | Scheer .......... 705/26 |
| 2003/0015585 A1 | 1/2003 | Wike, Jr. et al. |
| 2003/0061129 A1 | 3/2003 | Todd et al. |
| 2004/0009465 A1 | 1/2004 | Luckanatinvong |
| 2004/0031274 A1 | 2/2004 | Cho et al. |
| 2004/0035123 A1 | 2/2004 | Kim et al. |
| 2004/0100380 A1 | 5/2004 | Lindsay et al. |
| 2004/0253733 A1 | 12/2004 | Prusik et al. |
| 2004/0254759 A1 | 12/2004 | Kubach et al. |
| 2005/0008539 A1 | 1/2005 | Matsuura et al. |
| 2005/0082376 A1 | 4/2005 | Lubow et al. |
| 2005/0086108 A1 | 4/2005 | Sakamoto et al. |
| 2005/0132725 A1 | 6/2005 | Menten et al. |
| 2005/0155372 A1 | 7/2005 | Dentella et al. |
| 2005/0171854 A1 | 8/2005 | Lyon |
| 2005/0258961 A1 | 11/2005 | Kimball et al. |
| 2006/0006999 A1 | 1/2006 | Walczyk et al. |
| 2006/0055530 A1 | 3/2006 | Wang et al. |
| 2006/0119484 A1 | 6/2006 | Chishima et al. |
| 2006/0171570 A1 | 8/2006 | Brendley et al. |
| 2006/0178947 A1 | 8/2006 | Zsigmond et al. |
| 2006/0190363 A1 | 8/2006 | Brown et al. |
| 2006/0199155 A1 * | 9/2006 | Mosher .......... 434/127 |
| 2006/0210115 A1 | 9/2006 | Nemet |
| 2006/0237427 A1 | 10/2006 | Logan |
| 2007/0016852 A1 | 1/2007 | Kim et al. |
| 2007/0035380 A1 | 2/2007 | Overhultz et al. |
| 2007/0046552 A1 | 3/2007 | Marino |
| 2007/0103304 A1 | 5/2007 | Newton et al. |
| 2007/0251521 A1 | 11/2007 | Schackmuth et al. |
| 2008/0047282 A1 | 2/2008 | Bodin et al. |
| 2008/0052037 A1 | 2/2008 | Bodin et al. |
| 2008/0052200 A1 | 2/2008 | Bodin et al. |
| 2008/0052201 A1 | 2/2008 | Bodin et al. |
| 2008/0052202 A1 | 2/2008 | Bodin et al. |
| 2008/0055084 A1 | 3/2008 | Bodin et al. |
| 2008/0094214 A1 | 4/2008 | Azevedo et al. |
| 2009/0099943 A1 | 4/2009 | Bodin et al. |
| 2011/0163846 A1 | 7/2011 | Bodin et al. |

FOREIGN PATENT DOCUMENTS

| | | |
|---|---|---|
| WO | 2005015510 A1 | 2/2005 |

OTHER PUBLICATIONS

Lindsay et al., "Ratial RFID Systems Without Smart Shelves", 2003, pp. 1-13, retrieved May 30, 2006 http://www.jefflindsay.com/rfid1.shtml.

Gilbert, "Major retailers to test smart shelves", ZDNet News: Jan. 8, 2003, pp. 1-6, retrieved May 31, 2006 http://news.zdnet.com/2100-9584_22-979710.html.

"itag", iTAG RFID—Smart Shelf, AC/Corporation, pp. 1-2, 2003-2006, retrieved May 12, 2006, http://www.ac-corporation.com.ph/products/iTAG/solutions/shelves.asp.

"Automated Livestock management with RFID-Driven Production Systems—15 Years of Work Applying RFID Technology to the Real World", Osborne Industries Inc., 2005, pp. 1-26.

USPTO Office action for related U.S. Appl. No. 11/467,214 dated Sep. 2, 2009.

USPTO Notice of Allowance for U.S. Appl. No. 11/467,187 dated Oct. 21, 2009.

USPTO office action for U.S. Appl. No. 11/467,214 dated Mar. 18, 2010.

USPTO Notice of Allowance for U.S. Appl. No. 11/467,195 dated Jul. 23, 2010.

USPTO Office Action for U.S. Appl. No. 11/467,214 dated Jul. 21, 2010.

USPTO Office Action regarding U.S. Appl. No. 11/467,187, dated Mar. 9, 2009.

USPTO Office Action regarding U.S. Appl. No. 11/467,195, dated Sep. 10, 2008.

USPTO Final Office Action regarding U.S. Appl. No. 11/467,195, dated Mar. 4, 2009.

USPTO Office Action regarding U.S. Appl. No. 11/467,195, dated Jul. 27, 2009.

USPTO Notice of Allowance regarding U.S. Appl. No. 11/467,195, dated Feb. 5, 2010.

USPTO Office Action regarding U.S. Appl. No. 11/467,200, dated Sep. 11, 2008.

USPTO Final Office Action regarding U.S. Appl. No. 11/467,200, dated Mar. 10, 2009.

USPTO Appeal Brief regarding U.S. Appl. No. 11/467,200, dated Apr. 28, 2009.

USPTO Notice of Allowance regarding U.S. Appl. No. 11/467,200, dated Aug. 12, 2009.

USPTO Office Action regarding U.S. Appl. No. 11/467,203, dated Oct. 21, 2008.

USPTO Final Office Action regarding U.S. Appl. No. 11/467,203, dated Mar. 26, 2009.

USPTO Appeal Brief regarding U.S. Appl. No. 11/467,203, dated Apr. 24, 2009.

USPTO Examiners Answer regarding U.S. Appl. No. 11/467,203, dated Aug. 13, 2009.

USPTO Decision on Appeal regarding U.S. Appl. No. 11/467,203, dated May 2, 2011.

USPTO Notice of Allowance regarding U.S. Appl. No. 11/467,203, dated May 27, 2011.

USPTO Notice of Allowance regarding U.S. Appl. No. 11/467,214, dated Dec. 28, 2010.
USPTO Office Action regarding U.S. Appl. No. 11/467,224, dated Jun. 27, 2008.
USPTO Notice of Allowance regarding U.S. Appl. No. 11/467,214, dated Sep. 22, 2008.

USPTO Office Action regarding U.S. Appl. No. 12/341,884, dated Oct. 21, 2010.
USPTO Notice of Allowance regarding U.S. Appl. No. 12/341,884, dated Feb. 9, 2011.

* cited by examiner

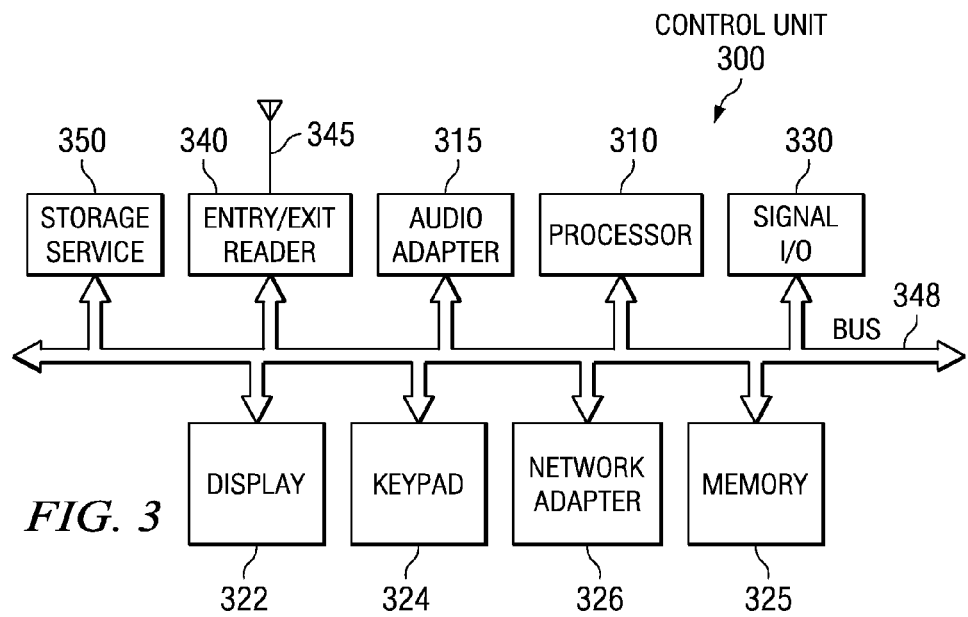
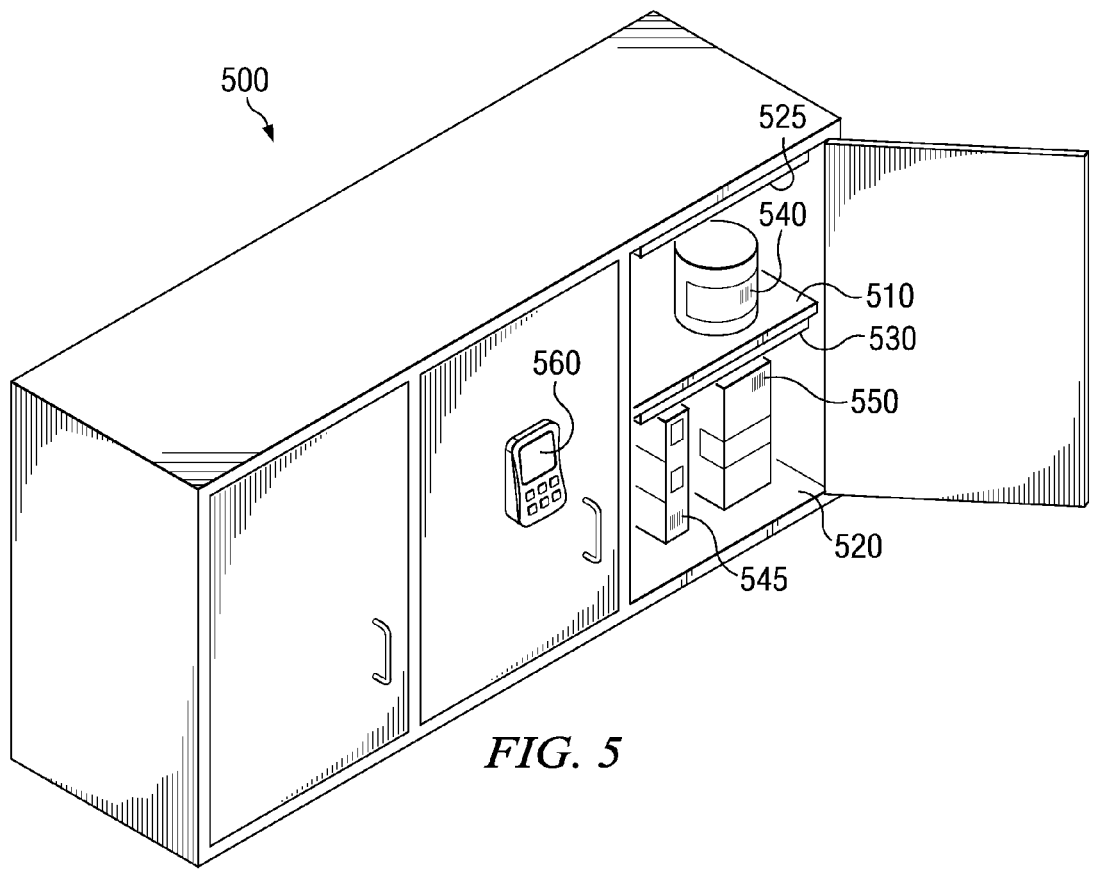

FIG. 9

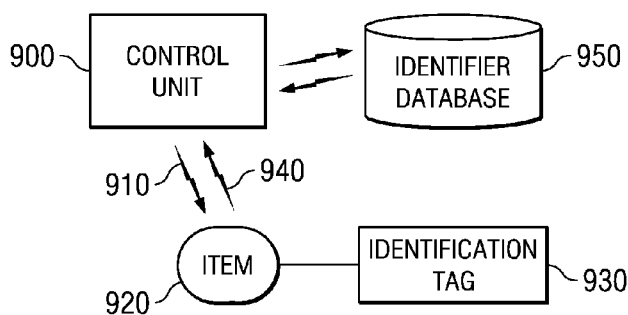

FIG. 10

| MEAL PLAN 1 | INGREDIENTS | | NUTRITIONAL INFORMATION | |
|---|---|---|---|---|
| | NAME | MEASURE | | |
| CHICKEN AND RICE | OIL | 1 TBSP | CALORIES | 410 |
| | CHICKEN | 4 EACH | TOTAL FAT | 10 g |
| | CREAM OF CHICKEN SOUP | 1 CAN | CHOLESTEROL | 65 mg |
| | | | SODIUM | 660 mg |
| | WATER | 1 ½ CUPS | CARBOHYDRATE | 46 g |
| | RICE | 2 CUPS | PROTEIN | 33 g |

| MEAL PLAN 2 | INGREDIENTS | | NUTRITIONAL INFORMATION | |
|---|---|---|---|---|
| | NAME | MEASURE | | |
| APPLE COBBLER | APPLES | 4 MED | CALORIES | 258 |
| | WATER | 1 CUP | TOTAL FAT | 10 g |
| | CINNAMON | 2 TSP | CHOLESTEROL | 1 mg |
| | CORNSTARCH | 2 TBSP | SODIUM | 83 mg |
| | SUGAR | ¼ CUP | CARBOHYDRATE | 41 g |
| | FLOUR | 1 CUP | PROTEIN | 4 g |
| | BAKING POWDER | 1 TSP | | |
| | CANOLA OIL | ¼ CUP | | |
| | HONEY | ¼ CUP | | |
| | BUTTERMILK | ½ CUP | | |

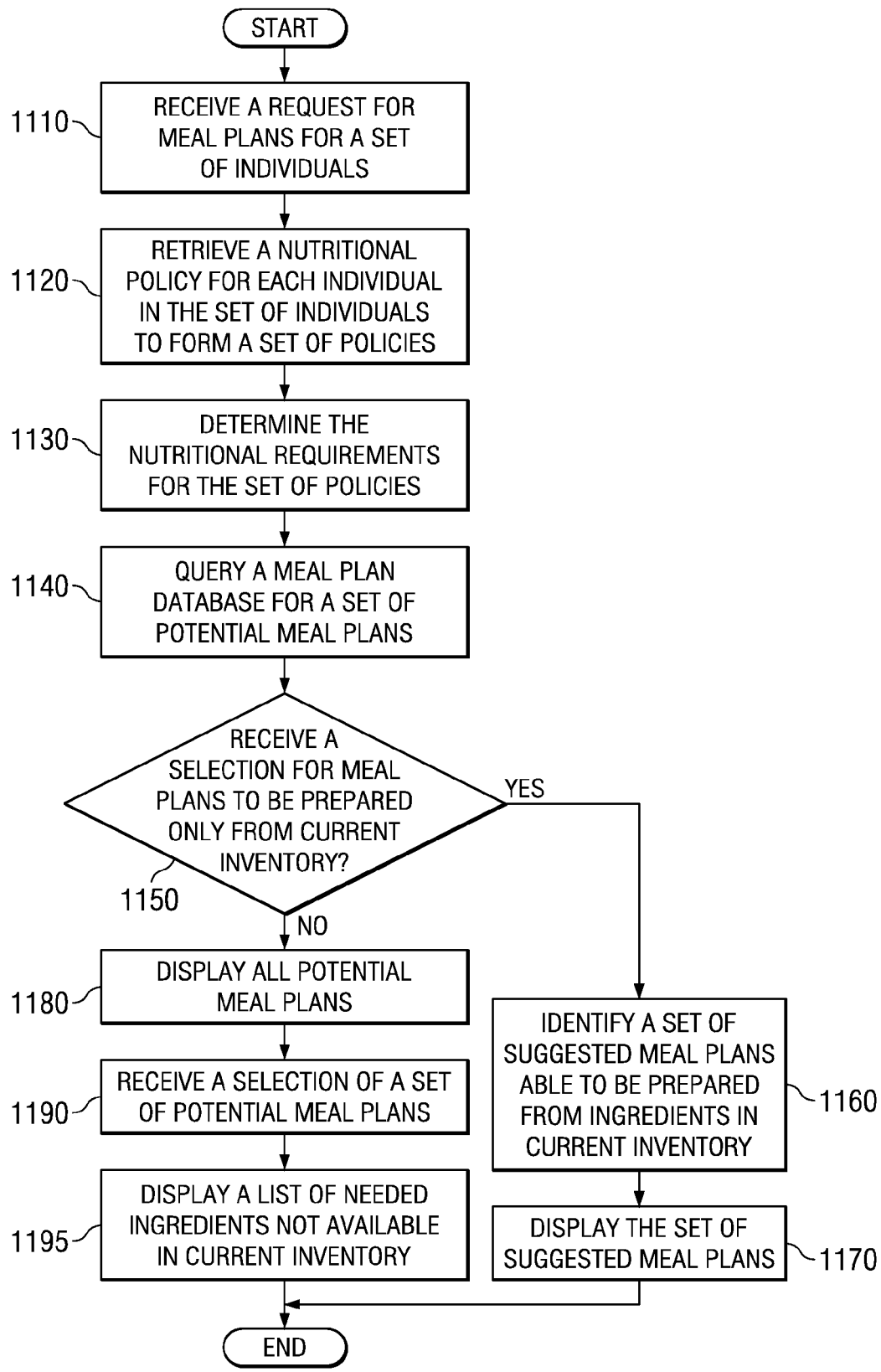

GENERATING POLICY DRIVEN MEAL PLANS

BACKGROUND

1. Field of the Invention

The present application relates generally to an improved data processing system, and in particular to a method and apparatus for meal planning. Still more particularly, the present invention is directed to a computer implemented method, an apparatus, and computer program product for generating policy driven meal plans based on a current inventory.

2. Description of the Related Art

Today, each member of a family frequently has their own unique diet policy. A diet policy is a set of dietary requirements/restrictions that make up a given diet. For example, the husband is an athlete trying to build muscle. Therefore, the husband will be on a high protein diet policy. The wife is on a doctor recommended low cholesterol and/or low sodium diet. The child is a diabetic and must adhere to a low sugar diet policy. In a family with multiple diverse diet policies such as this, meal planning and preparation can become incredibly complex. A user must determine one or more meals that will satisfy the combined diet policies' nutritional requirements and food restrictions for each family member. Frequently, a user will be forced to prepare multiple separate meals to satisfy the multiple diet policies due to the difficulties of coming up with a single meal to satisfy multiple diet policies.

Although users can consult diet/recipe books to obtain recipes to meet the requirements of a particular diet, a diet/recipe book will generally only provide recipes for a single diet policy. Manually searching for recipes that satisfy multiple different diet policies can be time consuming and burdensome.

In addition, preparing the meal(s) that satisfy multiple diverse diet policies can be difficult where a user is uncertain as to which ingredients are available in inventory, what amounts of those ingredients are available in inventory, and which ingredients need to be purchased/replaced. For example, refrigerators and cabinets are frequently overfilled with too many items. In such a case, a user may be unable to determine what ingredients are in inventory due to obscuring of one or more items behind multiple other items. In addition, empty or almost empty containers left in a refrigerator or cabinet can lead a user to believe that an ingredient, such as milk, is available in stock when in fact, there is an insufficient amount of that ingredient remaining to satisfy the measure requirements of a recipe.

SUMMARY

The aspects of the illustrative embodiments provide a computer implemented method, apparatus, and computer usable program product for generating meal plans based on a set of nutritional polices. The process determines nutritional requirements specified by a set of nutritional policies in response to receiving a request for a set of meal plans for a set of users. The set of nutritional policies correspond to the set of users. The process identifies a set of potential meal plans in response to determining the nutritional requirements specified by the set of nutritional policies. Each potential meal plan in the set of potential meal plans satisfies all nutritional requirements for the set of nutritional policies. The process generates a listing of ingredients required by the selected meal plan that is unavailable in a current inventory in an amount required by the selected meal plan, in response to receiving a selection of a potential meal plan to form a selected meal plan.

BRIEF DESCRIPTION OF THE DRAWINGS

The novel features believed characteristic of the illustrative embodiments are set forth in the appended claims. The illustrative embodiments themselves, however, as well as a preferred mode of use, further objectives and advantages thereof, will best be understood by reference to the following detailed description of the illustrative embodiments when read in conjunction with the accompanying drawings, wherein:

FIG. 3 is a block diagram of a control unit in accordance with an illustrative embodiment;

FIG. 5 is a block diagram of a cabinet including a set of mass sensor shelves and item identifiers in accordance with an illustrative embodiment;

FIG. 9 is a block diagram illustrating an interaction of a user interface and tag reader with an identification tag in accordance with an illustrative embodiment;

FIG. 10 is a block diagram illustrating meal plans in accordance with an illustrative embodiment; and FIG. 11 is a flowchart illustrating a process for selecting a meal plan based on a set of policies in accordance with an illustrative embodiment.

DETAILED DESCRIPTION OF THE PREFERRED EMBODIMENT

Figure 1:
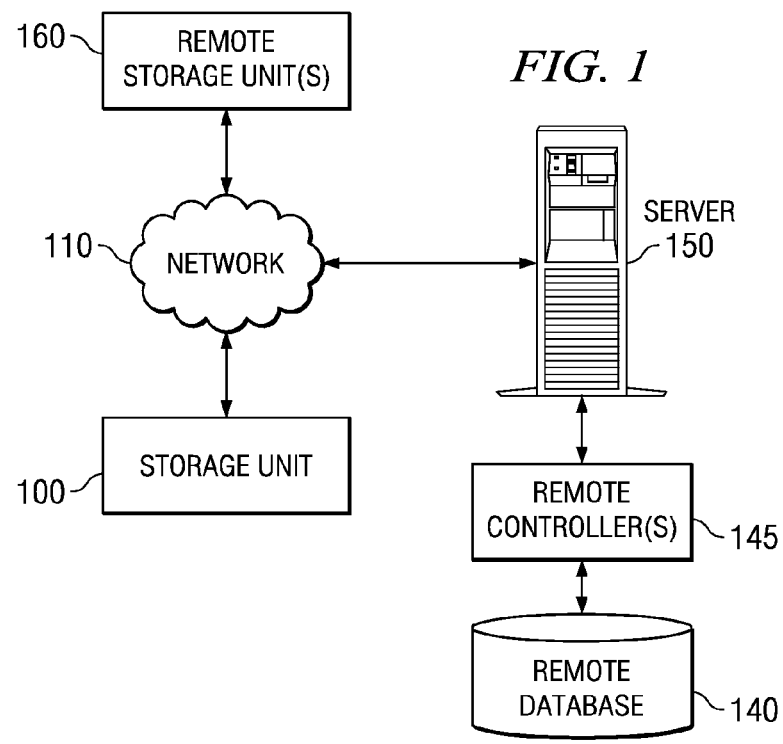
FIG. 1 is a pictorial representation of a network of storage units in accordance with an illustrative embodiment.

Today, each member of a family frequently has their own unique diet policy. For example, the husband is an athlete trying to build muscle. Therefore, the husband will be on a high protein diet policy. The wife is on a doctor recommended low cholesterol and/or low sodium diet. The child is a diabetic and must adhere to a low sugar diet policy. In a family with multiple diverse diet policies such as this, meal planning and preparation can become incredibly complex. The illustrative embodiments recognize the need for a system that can generate meal plans that meet the requirements of all the diet/nutritional policies in a family from a list of available inventory.

Therefore, the illustrative embodiments provide a computer implemented method, apparatus, and computer usable program product for generating meal plans based on a set of nutritional polices. The process receives a request for meal plans for a set of users. The process determines nutritional requirements specified by the set of nutritional policies. The set of nutritional policies has one or more policies and correspond to the set of users that has one or more users.

The process identifies a set of potential meal plans. Each potential meal plan in the set of potential meal plans satisfies all nutritional requirements for the set of nutritional policies. The process generates a listing of ingredients required by the selected meal plan that is not available in a current inventory in an amount required by the selected meal plan, in response to receiving a selection of a potential meal plan to form a selected meal plan.

Current inventory is a record or listing of all the consumable items available in stock. Current inventory includes an identification identifying each consumable item in stock and a measure/amount of each item in stock. Items in inventory are generally stored in storage units. As used herein, a storage unit is an appliance, room, or repository for storing and/or displaying items. A storage unit typically includes shelves or compartments to hold and/or organize items. A storage unit includes, but is not limited to, a refrigeration unit, a pantry, a storeroom, a cabinet, a set of shelves, a cupboard, a boxcar, a trailer, an oven and/or any other compartment or container having space for storing and/or displaying items.

As used herein, a consumable item is any item that is depleted through use. Consumable items include, but are not limited to, food items, beverage items, soap, detergents, medicine, disposable paper products, and/or any other item that is depleted through use. Consumable items are generally consumed or depleted on a regular or semi-regular basis and then replaced and/or replenished by users in order to maintain a supply of these items in an inventory.

The items present in an inventory can be identified using a Universal Product Code. A Universal Product Code (UPC) is a machine readable bar code coupled with a human-readable Universal Product Code number. The Universal Product Code includes is a six-digit manufacturer identification number that provides information regarding a product, such as the manufacturer identification and product item number. A unique universal product code is not assigned to more than one product. Thus, a Universal Product Code scanner can read a Universal Product Code associated with a particular product to identify the product and/or determine a non-depletion quantity for the item. However, to maintain current inventories, each item in an inventory must be manually scanned with a bar code reader.

A Universal Product Code can provide a non-depleted amount of an item, such as a net weight of the item at the time of purchase. However, Universal Product Code cannot be used to monitor the amount of a consumable item available in a current inventory after the item is opened for use.

Radio frequency identification (RFID) can be used to identify, locate, and track items in an inventory. Radio frequency identification systems utilize radio frequency identification readers and radio frequency identification tags to identify objects associated with a radio frequency identification tag.

A radio frequency identification reader is a device that includes a transmitter and a receiver. Radio frequency identification tags, also referred to as transponders, identification tags, or smart tags, are small integrated circuits coupled with an antenna to transmit data. A radio frequency identification tag can be attached to or incorporated into an item package or into the item itself.

A radio frequency identification reader transmits an interrogate signal to radio frequency identification tags within an interrogate zone of the reader. Multiple radio frequency identification tags can reside within an interrogate zone of a radio frequency identification reader. In response to receiving an interrogate signal, radio frequency identification tags transmit a radio frequency response signal to the reader via an antenna associated with the tag. The response signal typically includes identification data, such as an identification code. The reader receives the radio frequency response transmissions from the identification tags. The reader can identify a product based on the identification code included in the response signal. The reader can also estimate an approximate location of the tag based on the strength and direction of the response signal.

Each radio frequency identification tag in the interrogate zone can be individually recognized by the radio frequency identification tag reader based on the identification codes transmitted by each tag. Thus, a radio frequency identification tag reader can take an entire inventory of all items within an interrogate zone having a radio frequency identification tag without requiring intervention of a human user. However, radio frequency identification cannot be utilized to determine a meal plan based on the current amount of an item in inventory after the item has been opened/partially depleted by use.

FIG. 1 is a pictorial representation of a network of storage units in which the illustrative embodiments may be implemented in accordance with an illustrative embodiment. Storage unit 100 is a storage unit having an inventory of consumable items. Storage unit is connected to network 110. Network 110 is a medium used to provide communications links between various devices, databases, and storage units connected together, such as storage unit 100, remote storage unit(s) 160, and remote database 140. Network 110 may include connections, such as wire, wireless communication links, or fiber optic cables.

Storage unit 100 connects to network 110 along with one or more remote storage unit(s) 160. In addition, remote databases(s) 140 and remote controller(s) connect to network 110 via one or more servers, such as server 150. In the depicted example, server 150 provides data, such as boot files, operating system images, and applications to remote controller(s) 145 and remote storage unit(s) 160. Network 110 may include additional servers, clients, and other devices not shown.

Figure 2:
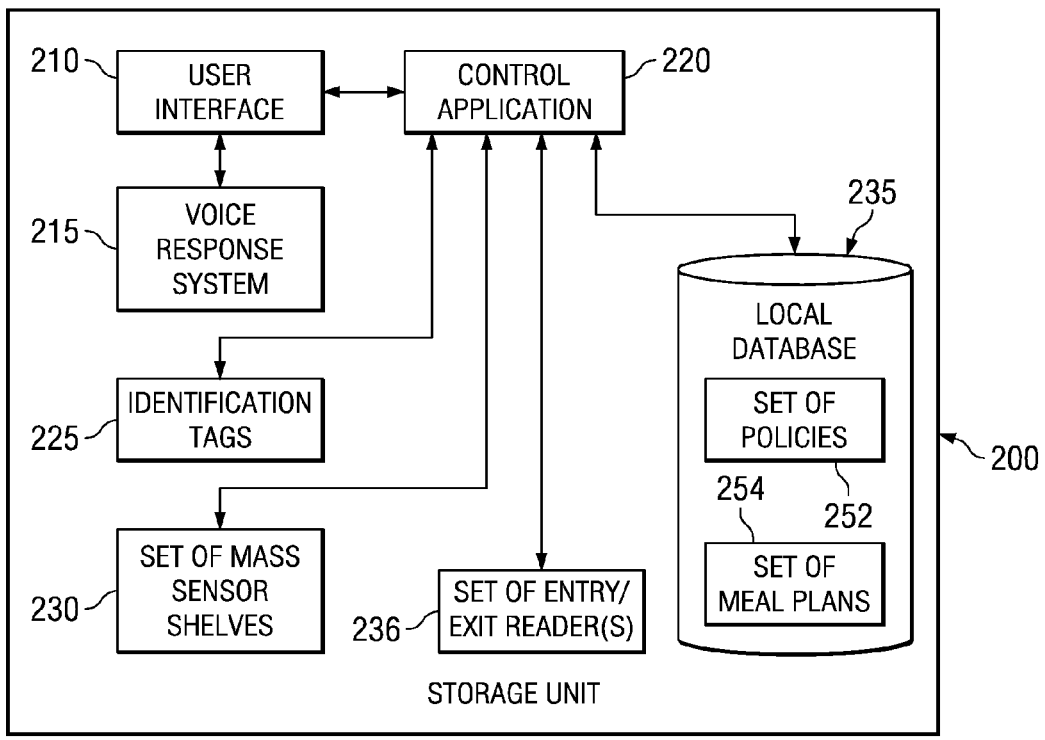
FIG. 2 is a pictorial representation of a storage unit in accordance with an illustrative embodiment.

FIG. 2 is a pictorial representation of a storage unit in accordance with an illustrative embodiment. Storage unit 200 is a storage unit, such as storage unit 100 and remote storage unit(s) 160 in FIG. 1.

User interface 210 provides a digital display for providing output to a user, as well as a keypad and/or touch screen for receiving input from a user. User interface 210 is associated with voice response system 215. Voice response system 215 includes a microphone, speaker, and voice synthesizer. Voice response system 215 permits users to provide verbal input to control application 220. Voice response system 215 also permits users to receive verbal output from control application 220, such as in providing text to speech operations.

Control application 220 is an application for receiving input and sending output to a user via user interface 210. Control application 220 identifies items associated with an identification tag placed in storage unit 200 to determine what ingredients are available in current inventory.

Items in inventory are identified via set of identification tags 225. Set of identification tags 225 is a set of one or more identification tags associated with one or more items in storage unit. Each identification tag has a unique item identification code associated with the identification tag. In this illustrative example, set of identification tags 225 is a set of radio frequency identification tags associated with a set of consumable items inside storage unit 200.

Set of item identifier(s) 236 is a set of one or more item identifier(s). Item identifiers are used to identify an item as well as to determine an approximate location of an item and a precise location of an item. An approximate location of an item can be determined by a single item identifier. The item identifier receives a response signal from an identification tag. Control application 220 can determine an approximate location of the identification tag based on the strength and direction of the response signal. The item identifier generates approximate location coordinates for the approximate location of the identification tag. An item identifier in set of item identifier(s) 236 can be implemented by a radio frequency identification tag reader, a Universal Product Code scanner, or any other device for obtaining information from an identification tag. In an example in which the item identifier is a Universal Product Code scanner, a user scans each item at the Universal Product Code scanner. In an alternative example, a user can manually enter an identification code, item identifier, or other item description at a user interface rather than utilizing an item identifier.

Control application 220 can request an approximate location of the identification tag from an item identifier in set of item identifiers 236. In response, the item identifier generates approximate location coordinates for the approximate location of the identification tag based on the strength and direction of the response signal received by a given item identifier. The given item identifier than transmits this location to control application 220. In the alternative, the approximate location can be stored in local database 235.

Control application 220 can determine a precise location by triangulating a set of approximate coordinates generated by two or more item identifiers in set of item identifiers 236. The triangulated coordinates form a set of precise coordinates for the precise location of the identified item in storage unit 200. The precise location of the item can be stored in a database, such as local database 235 or remote database 140 in FIG. 1.

Control application 220 also determines a current amount of each identified item in storage unit 200 based on mass data for each identified item received from set of mass sensor shelves 230. Set of mass sensor shelves 230 is a set of one or more customized shelves having a mass sensor grid on an upper surface of the shelf. Each mass sensor associated with a mass sensor shelf is an independent sensor capable of measuring a mass of an object resting on the mass sensor. Each mass sensor transmits mass sensor measurements in the form of mass sensor data to control application 220.

Control application 220 stores mass footprint data, mass sensor data, item identification data, and meta information for each item stored in storage unit 200 in a local database 235 and/or remote database(s), such as remote database(s) 140 in FIG. 1. Mass sensor data for an identified item includes a current mass for an item, a prior mass for the item, an initial mass for the item, a depleted mass for the item, and a non-depleted mass for the item. A current mass is the most recent mass measurement for the item. The prior mass for the item is the previous mass for an item. The initial mass is the first mass measurement for the item when the item is identified by control application 220 for the first time. The depleted mass is the tare or mass of the item's empty container. In other words, the depleted mass is the mass of the item after the contents or product has been completely consumed and the empty item container is all that remains.

Control application 220 monitors mass sensor data and meta information for each item based on the mass sensor data, meta information, and item identification information stored in local database 235 and/or remote databases. Meta information includes details like timestamps associated with an item expiration data, a data and/or time when an item is first detected entering a storage unit, a time when an item is removed from a storage unit, a time interval between a time when an item is removed from a storage unit and the time when the item is returned to the storage unit, and any other time and/or data information relevant to an item freshness, perishability, and expiration information. Meta information is associated with each identified item stored in storage unit 200. Thus, control application 220 can provide a warning or alert when an item is past its expiration date and/or no longer fit for human consumption due to the age of the item.

Local database 235 is any type of known or available data storage device. In this illustrative example, local database 235 is depicted as a database located on storage unit 200. However, local database 235 can also include any secondary data storage device and/or a remote data storage device, such as remote database 140 in FIG. 1. Local database 235 can be a single data storage device or multiple data storage devices. Local database 235 is a storage device for storing nutritional policies for a plurality of users and a plurality of updateable meal plans.

Set of policies 252 is a set of policies corresponding to a set of users. When a user requests one or more meal plans, the user identifies two or more individual users. Control application 220 retrieves a nutritional policy for each identified user to form set of policies 252. Each nutritional policy in set of policies 252 includes a listing of nutritional requirements for the corresponding user as well as dietary restrictions. Control application 220 determines a set of potential meal plans conforming to a set of policies by comparing the nutritional requirements of each nutritional policy in the set of policies with the nutritional information corresponding to each meal plan.

Thus, in this illustrative example, control application activates set of item identifiers 236 when control application detects a door of storage unit 200 is opened. An item identifier transmits an interrogate signal. The item identifier identifies an item based on a response signal received from an identification tag associated with the item as the item enters storage unit 200 to form an identified item. The item identifier(s) also determine an approximate and/or exact location for the identified item based on the response signal.

Control application 220 determines the location of the item based on a mass footprint of the item generated when the item is placed on a given mass sensor shelf. The item's mass footprint is an impression of a portion of the item in contact with a mass sensor shelf. If two or more items are placed in the storage unit with a time interval occurring between placement of the items inside the storage unit, control application 220 associates a first change in mass data with the first item identified entering the storage unit. Control application 220 associates a second change in mass data with an item identified entering the storage unit second in time. Control application 220 utilizes the change in mass data to create a mass footprint and determine a current mass for the item identified immediately prior in time to the change in mass data.

If two or more items are identified entering the storage unit at the same time with no time interval in between the two items, control application 220 will associate a change in mass sensor data with the identified item having a corresponding mass footprint. For example, if a user places a jar of peanut butter and a carton of orange juice 200 at the same time, control application 200 will associated mass footprint data indicating a round mass footprint with the jar of peanut butter and associated mass footprint data indicating a square mass footprint with the carton of orange juice. Thus, control application 220 can distinguish items placed inside storage unit 200 simultaneously based on mass footprint data, such as the shape of the mass footprint.

If a user places two or more items in storage unit 200 at the same time that have similar mass footprint data, such as a jar of peanut butter and a jar of jelly, control application 220 will generate an error message and/or prompt a user to indicate a location and/or an identification of each item placed in the storage unit simultaneously.

In an alternative embodiment, control application 220 determines precise coordinates for the location of an identified item by triangulating location data received from two or more location sensors. In this example, location sensors are radio frequency identification readers.

Control application 220 requests mass sensor data associated with a location for the identified item. Control application 220 determines a current amount of the identified item by subtracting a current mass for the item from a non-depleted mass for the item. The item identification data and mass data are stored in database 235. In this manner, control application 220 maintains a current real-time inventory of all ingredients available and the amounts or quantity of each ingredient available in inventory. Control application 220 stores the current inventory, including the amounts of each item in inventory, in local database 235.

Control application 220 stores mass sensor data and item identification data for each item in storage unit in local database 235. Mass sensor data for an identified item includes a current mass for an item, a prior mass for the item, an initial mass for the item, a depleted mass for the item, and a non-depleted mass for the item. A current mass is the most recent mass measurement for the item. The prior mass for the item is the previous mass for an item. The initial mass is the first mass measurement for the item when the item is identified by control application 220 for the first time. The depleted mass is the tare or mass of the item's empty container. In other words, the depleted mass is the mass of the item after the contents or product has been completely consumed and the empty item container is all that remains. Thus, the net weight of the item is the depleted mass of the item subtracted from the gross weight of the item. The non-depleted mass is the net weight of the item. The non-depleted mass is a predetermined/predefined quantity of an item prior to use by a consumer. In other words, a non-depleted mass of a consumable item is the mass of the item at the time the item is purchased in an original unused condition. In an alternative embodiment, the non-depleted mass can be calculated by subtracting the item's tare weight from the item's initial or gross weight.

Control application 220 monitors real-time depletion of each identified item in storage unit 200 by comparing current mass measurements for each item with a non-depleted mass for the item. When the current mass of an identified item reaches a threshold depletion, the item is identified as a depleted item. Control application 220 provides a notification to a user to replace and/or replenish depleted items via user interface 210.

The threshold depletion is a user defined depletion level. The threshold depletion indicates a threshold amount of an item remaining in an item container. The determination as to whether a depletion level has reached the threshold depletion for a given item is made based on a gross amount of an item remaining without subtracting a tare mass of an empty container. However, in this example, an accurate determination as to whether an item had reached the threshold depletion level may be inaccurate due to differences in container types. For example, a glass container has a greater mass than a plastic or cardboard container. Therefore, in another illustrative embodiment, a determination as to whether a depletion level has reached the threshold depletion for a given item is made based on a net amount of an item remaining after subtracting a tare mass of an empty container. In this manner, the affects of different container masses are taken into account when determining the current depletion of a given item.

When a user requests one or more meal plans for a set of users, control application 220 retrieves a nutritional policy for each user in the set of users. Each nutritional policy is retrieved from set of policies 252 in local database 235. Each policy specifies nutritional requirements and/or prohibitions consistent with a particular diet policy. For example, a policy for a diabetic would prohibit food items containing certain levels of sugars. A nutritional policy can be loaded into a system as an extensible markup language (XML) document that describes the nutritional needs of a particular individual.

Control application performs a search of set of meal plans 254 for meal plans conforming to a first policy in the set of policies 252 to form a first result set. Control application 220 performs a second search of set of meal plans 254 for meal plans conforming to the second policy in the set of policies 252 to form a second result set. Control application performs a search of set of meal plans 254 for conforming meal plans as to each policy in set of policies 252 until a result set has been generated for each policy in set of policies 252. As used herein, a conforming meal plan is a meal plan that satisfies all the nutritional requirements and prohibitions of a given nutritional policy.

Control application 220 selects meal plans that are included in the result set for every policy in set of policies. The meal plans that are included in every result set forms a set of potential meal plans. Control application 220 presents the set of potential meal plans to the user.

In response to receiving a selection of a potential meal plan, control application 220 compares the listing of required ingredients for the selected meal plan and the required measurements for each ingredient with the current inventory. Control application 220 generates a listing of all required ingredients that are not currently available in inventory in an amount required by the selected meal plan. This listing of needed ingredients is displayed to the user.

In an alternative embodiment, the user can select to display all conforming meal plans that can be completely prepared from ingredients available in the current inventory. In this case, control application 220 compares the required ingredients for each potential meal plan with the current inventory. Control application 220 identifies potential meal plans that can be completely prepared from ingredients in current inventory to form set of suggested meal plans. The set of suggested meal plans are presented to the user for selection.

In one example, control application 220 adds ingredients required by the selected meal plan but not available in a current inventory in an amount required by the selected meal plan to a shopping list for a user to purchase.

In another example, control application automatically sends a listing of the needed ingredients in the required amounts to a service that delivers new goods to the location of storage unit 200. For example, control application 220 can transmit a list of needed items to an online grocery provider having a goods delivery service via a network, such as network 110 in FIG. 1. The grocery provider delivers the needed item to a user's home for use in preparing one or more selected meal plans.

In another embodiment, a goods provider is able to gain access to storage unit 200 to deliver needed items without intervention by a user. For example, storage unit 200 can include a back door or access panel to permit a delivery person to restock storage unit 200 without requiring a presence of a user to provide access to storage unit 200. In this embodiment, control application determines which ingredients required by one or more selected meal plans are not available in current inventory. Control application 220 generates a list of the needed items, transmits the list to a goods delivery service, and the goods delivery service delivers and restocks storage unit 200 without requiring any action by a user.

In another illustrative embodiment, a user may fail to scan an item at a location sensor and/or one or more location sensors may be absent, malfunctioning or otherwise unavailable or unable to detect/identify items entering storage unit and exiting storage unit 200. In such a case, control application 220 can determine when an item is placed inside storage unit 200 and/or removed from storage unit 200 based on mass footprint data for items. Control application 220 uses the detection of item footprints for previously identified items to detect an item entry into storage unit 200 and/or the item exit/removal from storage unit 200. For example, if a user removes a jar of peanut butter and a carton of milk, control application 220 detects the removal of these two items based on the removal of the detected mass footprint on a mass sensor shelf associated with these items. In other words, when the two items are removed, the mass sensor data registered by the mass sensor shelf changes. Control application 220 can determine that the jar of peanut butter and the carton of milk were removed based on the absence of the footprint for the carton of milk and the footprint for the jar of peanut butter.

In this example, the user consumes some product from the carton of milk and jar of peanut butter then places the peanut butter and milk back into storage unit 200 within a configurable time interval. Control application 220 knows that two previously identified items were removed and two items with the same footprint have been added to storage unit 200. Control application 220 can check to ensure that the mass of the two items has not increased above the previous mass for the two removed items. Control application then correlates the items placed on the mass sensor shelf by matching the footprint of the two added items to the previously removed items. If mass for one of the items has increased, the increase in mass could indicate replenishing or adding to the contents of the item container. In addition, an increase in mass for an item could indicate a different item with the same footprint. In this case, re-identification or re-scanning of the item is necessary.

In one example in which re-identification is required, control application 220 will prompt user to enter an item identification for the item with the increased mass via a user interface or a voice response system. In this manner, control application 220 can identify/detect items that are not scanned and/or are not easily scanned on location sensors. An item could be difficult to scan if the item lacked radio frequency identification tags, the item identifier is a universal product code that must be manually scanned by a user, a user fails to scan an item, location sensors are malfunctioning, identification tags are malfunctioning, or location sensors and identification tags otherwise fail to provide an identification for the item. Thus, the illustrative embodiments permit triggering event handling of items based on a change in mass footprint data. A change in mass footprint data includes the appearance and disappearance of an item. Event handling of items includes depletion monitoring of items.

In this illustrative example, control application 220 is depicted as a separate component from item identifiers. However, in accordance with the illustrative embodiments, control application 220 can be combined with one or more item identifiers as a single component.

FIG. 3 is a block diagram of a control unit in accordance with an illustrative embodiment. A control unit is an application that monitors a current inventory, selects a set of potential meal plans based on a set of policies, and generates a list of needed ingredients not available in current inventory to prepare one or more selected meal plans. Control unit 300 is an example of hardware for implementing a control application, such as the control application 220 in FIG. 2.

Control unit 300 is hardware in which code or instructions implementing the processes of the illustrative embodiments may be located. Control unit 300 executes computer usable program code for controlling item identifiers, mass sensor shelves, and a user interface in accordance with the illustrative embodiments.

Processor 310, audio adapter 315, memory 325, display 322, keypad 324, network adapter 326, and signal input/output (I/O) 330 are connected via bus 348. Bus 348 may be comprised of one or more buses, such as a system bus and/or an I/O bus. Bus 348 may be implemented using any type of communications fabric or architecture that provides for a transfer of data between different components or devices attached to the fabric or architecture.

Processor 310 may include one or more processors or CPUs. Memory 325 may be a main memory, a read only memory (ROM), a random access memory (RAM), flash memory, a cache, or any other known or available memory for storing data, instructions, and/or computer usable program code. Controller 300 retrieves data, instructions, and/or code from memory, such as main memory or read only memory. In addition, controller 300 can retrieve data, instructions, and/or code from a remote memory location via a network connection.

Display 322 can include a touch screen display, an LED display, or any other type of known or available display for presenting output to a user or receiving input from a user. Keypad 324 is any type of known or available alphanumeric keypad for a user to provide input in the form of data, instructions, or program code to controller 300.

Network adapter 326 is coupled to the system to enable the data processing system to become coupled to other data processing systems or remote printers or storage devices through intervening private or public networks. Modems, cable modem and Ethernet cards are just a few of the currently available types of network adapters.

Signal input/output 330 includes one or more devices for sending and receiving signals to and from different components in a storage unit, such as a digital display and keypad, a touch screen, a voice recognition interface, an LED display, and/or any other known or available devices for sending and receiving input and output.

Item identifier 340 is an item identifier such as set of item identifier(s) 236 in FIG. 2. Item identifier 340 transmits an interrogate signal to determine an identification and/or location of identification tags within an interrogate zone of item identifier 340. Controller 300 is coupled to item identifier 340 via bus 348. Controller 300 activates item identifier 340 to transmit an interrogate signal to identify any radio frequency identification tags within an interrogate zone of item identifier 340. As used herein, an interrogate zone is a zone or region in which an interrogate signal has sufficient strength to be received by a radio frequency identification tag within the interrogate zone and trigger the radio frequency identification tag to transmit a radio frequency in response to the interrogate signal.

Storage device 350 is also optionally connected to bus 348. Storage device 350 may include any type of permanent and removable storage media. In addition, storage device 350 can include a remote storage device or storage provided by a storage service. Program code and instructions are located on storage device 350 and may be loaded into memory 325 for execution by processor 310.

The processes of the illustrative embodiments are preformed by processor 310 using computer implemented instructions, which may be located in memory 325. Processor 310, memory 325, signal input/output 330, and storage device 350 are functional components that can be implemented as functions in an application specific integrated circuit rather than using a processor paradigm.

Figure 4:
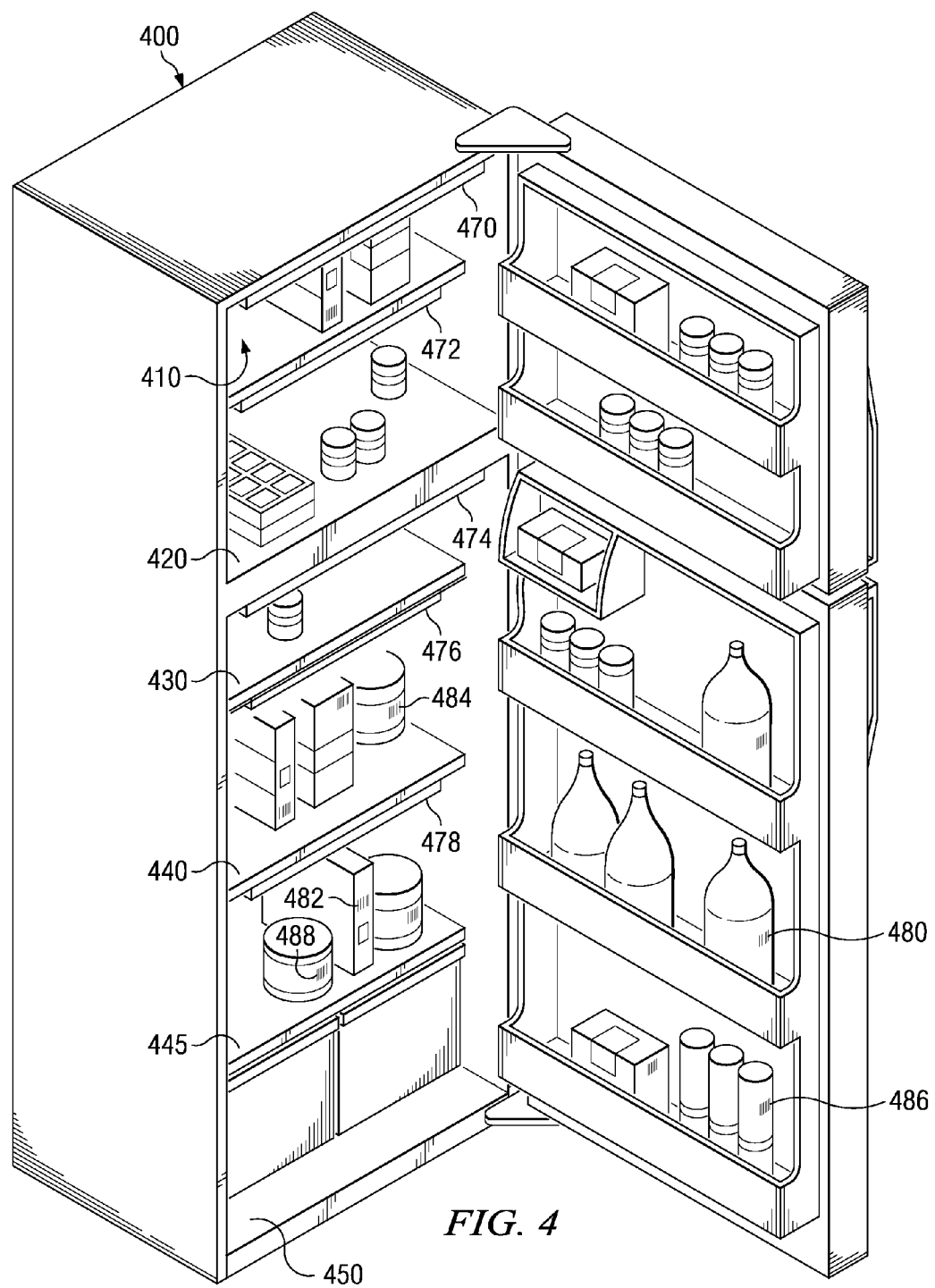
FIG. 4 is a block diagram of a refrigeration unit including a set of mass sensor shelves and item identifiers in accordance with an illustrative embodiment.

FIG. 4 is a block diagram of a refrigeration unit including a set of mass sensor shelves and item identifiers in accordance with an illustrative embodiment. As used herein, a refrigeration unit is any device, appliance, cabinet or room for storing food or any other substance at a lower temperature than room temperature. For example, a refrigeration unit includes a refrigerator, a freezer, a combination refrigerator and freezer, an ice box, a refrigerated railcar, a meat locker, an industrial refrigerator, an industrial freezer, a chest freezer, a reach-in cabinet, meat cases, frozen food cabinets, beverage coolers, food service carts, ice cream cabinets, soda fountain units, and any other known or available device or appliance for storing solid, semi-solid, or liquid items at a temperature lower than room temperature.

Refrigerator 400 is an example of a storage unit, such as storage unit 100 and remote storage unit(s) 120 in FIG. 1 and storage unit 200 in FIG. 2. Refrigerator 400 is any known or available type of refrigerator. In this illustrative example, refrigerator 400 is depicted as a consumer size refrigerator/freezer combination appliance. However, the illustrative embodiments are equally applicable to a refrigeration unit of any size, including, but not limited to, an apartment sized refrigerator/freezer, a room sized industrial refrigerator and/or a room-sized industrial freezer.

Refrigerator 400 includes a set of mass sensor shelves. As used here, a set of mass sensor shelves includes a single mass sensor shelf, as well as two or more mass sensor shelves. The set of mass sensor shelves includes mass sensor shelves 420-450. Each mass sensor shelf has a grid of mass sensors. Each mass sensor in the grid is capable of detecting a whole or partial mass of an object. The mass of an object is detected when an object is completely or partially resting on any portion of a mass sensor.

In accordance with the illustrative embodiments, a mass sensor shelf can be any surface having mass sensors that can hold or store an item. For example, mass sensor shelf 420 is a mass sensor shelf located in a freezer compartment of refrigerator 400. Mass sensor shelf 425 is a shelf in a door of the refrigerator. Mass sensor shelves 430-445 are mass sensor shelves located in a refrigerator compartment of refrigerator 400. Mass sensor shelf 450 is a mass sensor shelf located in the bottom of a drawer of refrigerator 400.

Refrigerator 400 includes a set of item identifiers, such as item identifiers 470-478. Item identifiers 470-478 are radio frequency identification readers. Item identifiers 470-478 identify an item entering or exiting refrigerator 400 based on information provided by an identification tag associated with the item.

Refrigerator 400 includes a variety of items stored within refrigerator 400. A number of the items have an identification tag associated with the item, such as identification tags 480-488. In accordance with this example, identification tags 480-488 are radio frequency identification tags.

In accordance with this illustrative embodiment, an item identifier is a separate component from a mass sensor shelf. However, in another embodiment, an item identifier is incorporated within the mass sensor shelf itself. In such a case, the mass sensor shelf is capable of transmitting an interrogate signal to radio frequency identification tags within an interrogate zone of the mass sensor shelf. The mass sensor shelf is also capable of receiving radio frequencies transmitted by radio frequency identification tags within a reception range of the mass sensor shelf.

Item identifiers 470-478 are automatically activated to scan for identification tags being placed inside and/or removed from a storage unit such as refrigerator 400, when a door to the storage unit is opened. In another example, item identifiers 470-478 are activated to scan for identification tags when a change in mass sensor data from a set of mass sensors occurs. In yet another alternative example, item identifiers 470-478 are activated on a periodic or cyclical basis to identify and locate items associated with identification tags 480-488.

In accordance with an alternative embodiment, identification tags, such as identification tags 480-488, are Universal Product Code bar codes and item identifiers, such as item identifiers 470-478, are Universal Product Code scanners. In this embodiment, a user manually scans identification tags, such as tag 480 at an item identifier, such as item identifier 478. Identification tag 480 is scanned by the user when the item is placed in the storage unit and/or removed from the storage unit. In this manner, the process of the illustrative embodiments can identify each item as the item is scanned for placement inside refrigerator 400.

In another example, an item is identified based only on a mass footprint for the item. For example, a jar of peanut butter can be identified based on the fact that a jar of peanut butter was removed from storage unit 200, a time interval passed, and a newly detected item having the same mass footprint as the peanut butter is placed on a given mass sensor shelf. If a user places a jar of peanut butter and a carton of orange juice in refrigerator 400 at the same time, the control application will associated mass footprint data indicating a round mass footprint corresponding to a jar of peanut butter as a current mass and footprint for the peanut butter. The control application will associate mass data indicating a square mass footprint corresponding to a carton of orange juice as a current mass and footprint for the carton of orange juice. Thus, the control application can distinguish items placed refrigerator 400 simultaneously based only on mass footprint data, such as the shape of the mass footprint.

If a user places two or more items in refrigerator 400 at the same time that have similar mass footprint data, such as a jar of peanut butter and a jar of jelly, the control application will require re-identification of the items. The control application will generate an error message and/or prompt a user to indicate a location and/or an identification to re-identify each of the items that were placed in the storage unit simultaneously. This illustrative embodiment in which an item is identified based on a mass footprint rather than scanning by an item identifier could be utilized in a system including, but not limited to, item identifiers that are Universal Product Code scanners that require manual scanning of each item and/or a user interface that requires a user to manually enter an item description/item identification for each item.

In another example, refrigerator 400 does not include a set of item identifiers. In this example, a user manually enters an item identification in a user interface prior to placing the item in refrigerator 400, as the user places the item in refrigerator 400, or after the user places in item in refrigerator 400. In this example, if a user does not enter an identification for an unidentified item, a user interface associated with refrigerator 400 will prompt the user to enter an item identification via the user interface.

FIG. 5 is a block diagram of a cabinet including a set of mass sensor shelves and item identifiers in accordance with an illustrative embodiment. Cabinet 500 is a storage unit, such as storage unit 100 and remote storage unit(s) 120 in FIG. 1 and storage unit 200 in FIG. 2.

Cabinet 500 includes a set of mass sensor shelves and a set of item identifiers. The set of mass sensor shelves includes mass sensor shelf 510 and mass sensor shelf 520. In this illustrative example, item identifiers 525-530 are radio frequency identification readers.

Each consumable item inside cabinet 500 has an identification tag, such as identification tags 540-550, associated with the item. In this example, item identifiers 525-530 are automatically activated to scan for items being placed inside cabinet 500 and items being removed from cabinet 500 when the cabinet door is opened.

User interface 560 is a digital display and keypad that provides output to a user and accepts input from the user. The digital display is any type of display for providing information to a user in the form of characters, numbers, symbols, or letters. The display can also include a touch screen for accepting input from a user. The keypad is an input device for data entry by a user. The keypad comprises alphanumeric keys and functional keys.

Figure 6:
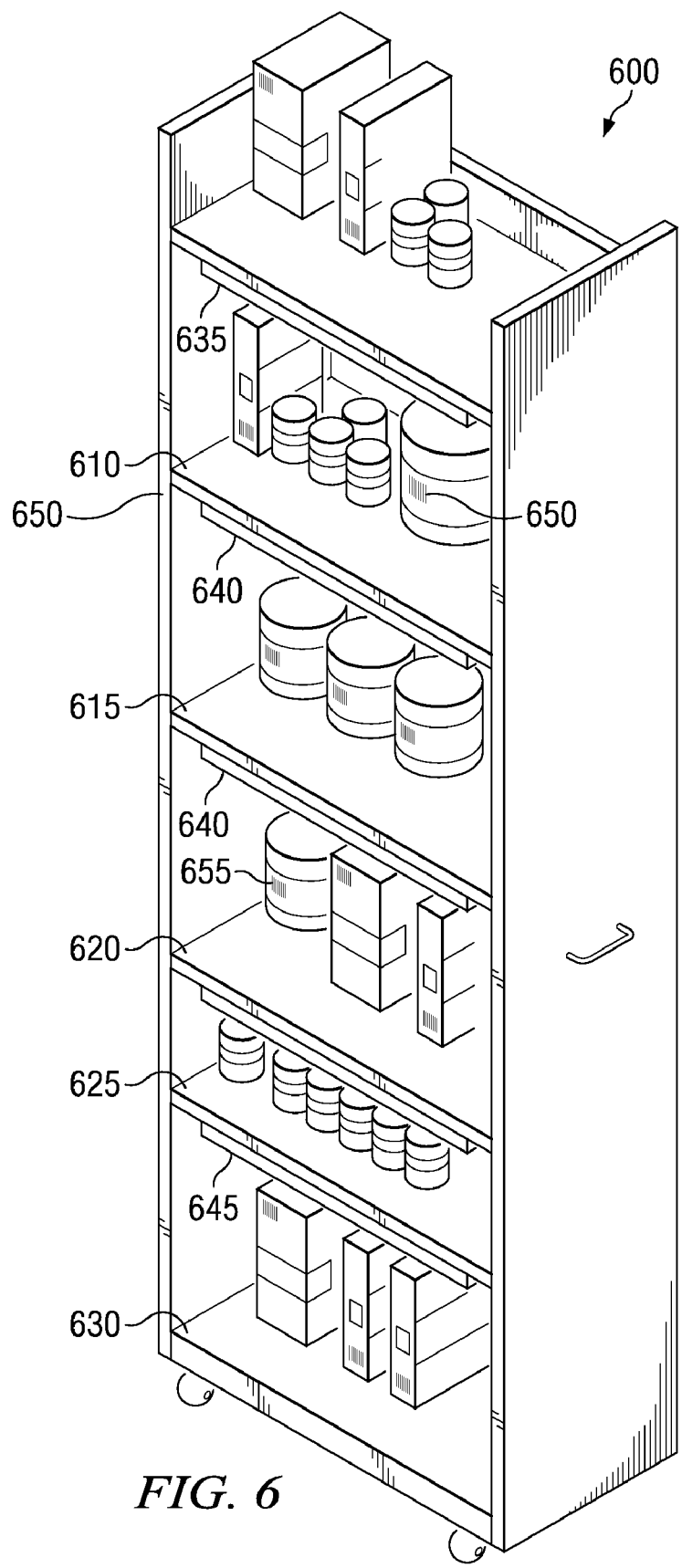
FIG. 6 is a block diagram of a set of shelves including mass sensor shelves and item identifiers in accordance with an illustrative embodiment.

FIG. 6 is a block diagram of a set of shelves including mass sensor shelves and item identifiers in accordance with an illustrative embodiment. Set of shelves 600 is a storage unit. Set of shelves 600 includes mass sensor shelf 610, mass sensor shelf 615, mass sensor shelf 620, mass sensor shelf 625, and mass sensor shelf 630.

Set of shelves 600 also includes item identifier 635, item identifier 640, and item identifier 645. In this example, item identifiers 625-630 are radio frequency identification readers. Item identifiers 635-645 are activated by the controller to transmit an interrogate signal to identification tags 650-655.

Those of ordinary skill in the art will appreciate that the storage units depicted in FIGS. 1-6 may vary. The depicted examples are not meant to imply architectural limitations with respect to an illustrative embodiment. For example, a storage unit in accordance with the illustrative embodiments could also include a pantry, a cupboard, a closet, a portable storage unit, or an oven. As used herein, an oven is a chamber or enclosed compartment for sterilizing, heating, warming, or cooking. An oven includes, but is not limited to, a stove, a kiln, a green house, a heated rail car, and/or a microwave oven.

Figure 7A:
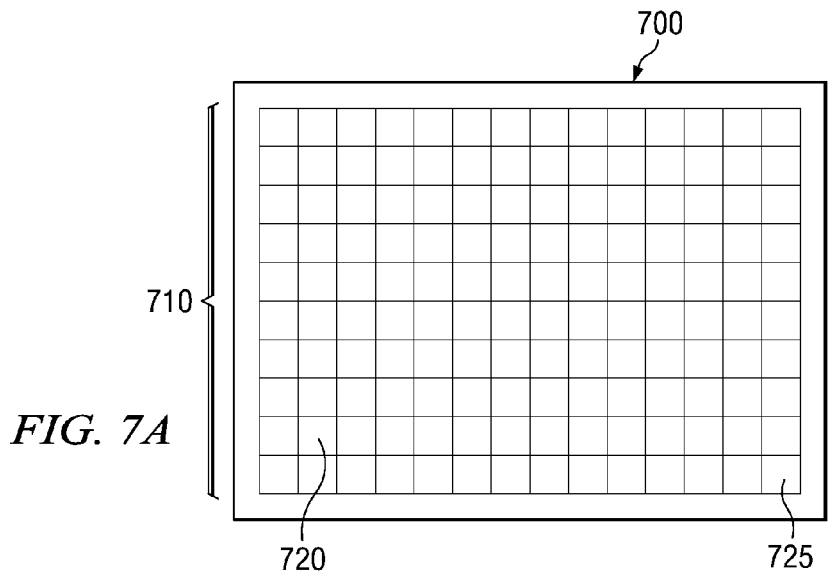
FIG. 7A is a block diagram of a mass sensor shelf having a mass sensor grid in accordance with an illustrative embodiment.

FIG. 7A is a block diagram of a mass sensor shelf having a mass sensor grid in accordance with an illustrative embodiment. Mass sensor shelf 700 is a mass sensor shelf inside a storage unit, such as refrigerator 400 in FIG. 4, cabinet 500 in FIG. 5, and set of shelves 600 in FIG. 6. Mass sensor shelf 700 has a mass sensor grid 710 spanning the entire area of an upper surface of mass sensor shelf 700. Mass sensor grid includes a plurality of mass sensors, such as mass sensor 720 and mass sensor 725.

Each block in mass sensor grid 710 represents an individual mass sensor in the plurality of mass sensors. Each sensor is separate and isolated from every other sensor in the mass sensor grid. In this illustrative example, mass sensors 720-725, are tiny mass sensors measuring one centimeter by one centimeter. In accordance with the illustrative embodiments, mass sensors can be any shape and any size mass sensors. For example, mass sensors 720-725 can measure one centimeter by two centimeters, or any other size.

Mass sensors in mass sensor grid 710 can measure a mass of an item wholly or partially placed on top of a given mass sensor. Thus, when an object is placed on a mass sensor shelf, each mass sensor covered by the object will generate mass data regarding a portion of the object. The process utilizes mass data from the set of mass sensors covered by an object on a mass sensor shelf to determine a mass of the object.

Figure 7B:
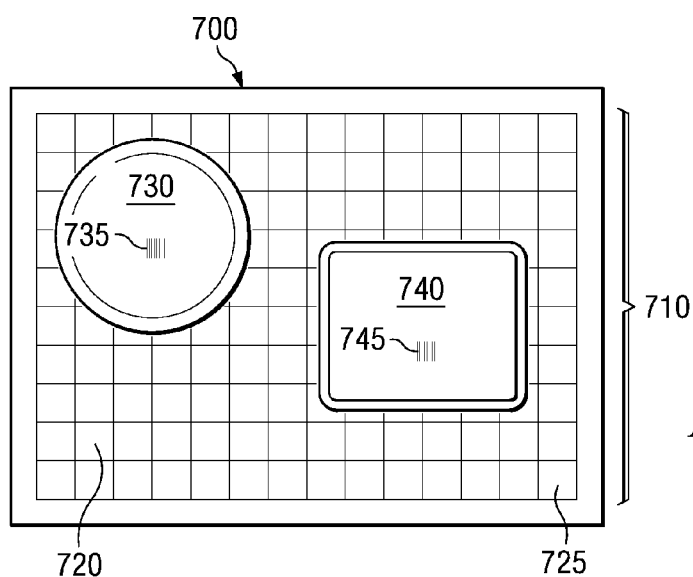
FIG. 7B is a block diagram of a mass sensor shelf having a mass sensor grid and consumable items on the shelf in accordance with an illustrative embodiment.

FIG. 7B is a block diagram of a mass sensor shelf having a mass sensor grid and consumable items on the shelf in accordance with an illustrative embodiment. Jar of peanut butter unit 730 is located on mass sensor shelf 700. Unit 730 rests on a set of mass sensors of mass sensor grid 710. The set of mass sensors generates mass data regarding the mass of unit 730. Unit 730 is associated with identifier tag 735. Identifier tag 735 is read by an item identifier to identify unit 730 as a jar of peanut butter.

In this example, a Tupperware of tuna salad is also located on mass sensor shelf 700. The Tupperware of tuna salad unit 740 is associated with identifier tag 745. An item identifier utilized identification data available from identifier tag 745 to identify unit 740 as a Tupperware of tuna salad. A set of mass sensors covered by unit 740 generate mass data regarding the mass of unit 740. Thus, when an object is placed on a mass sensor shelf, the object will rest on a set of mass sensors on the portion of the shelf covered by the object. Each mass sensor in the set of mass sensors transmits mass data regarding the mass of the object to a control application, such as control application 220 in FIG. 2.

The control application creates a mass footprint for the identified item. The mass footprint is an impression of a shape of a portion of the identified item in contact with a portion of the mass sensor shelf. The portion of the mass sensor shelf in contact with the identified item is the set of mass sensors transmitting mass data regarding the mass of the identified item. In this example, unit 730 has a mass footprint indicating a current mass of unit 730 and a shape of a surface of unit 730 in contact with mass sensor shelf 700. The shape indicated by the mass footprint is round. In this example, either the top or bottom of a jar of peanut butter is in contact with a portion of mass sensor shelf 700.

Likewise, the mass footprint for unit 740 indicates a current mass of unit 740 as well as a shape of a surface of unit 740 in contact with a portion of mass sensor shelf 700. In this example, unit 740 has a square shaped mass footprint, as a surface of the Tupperware of tuna salad in contact with mass sensor shelf 700 is square. In this case, the surface of the Tupperware of tuna salad in contact with a portion of mass sensor shelf could include a top, a bottom, or a side of a square Tupperware container.

In the illustrative embodiment shown in FIGS. 7A and 7B, the mass sensor shelf includes a grid array containing a mass sensor for each portion of the grid. The grid array determines a current mass for an item in contact with the grid array, as well as a mass footprint or impression of the portion of the item in contact with the grid array.

However, in another exemplary embodiment, the grid array includes a single mass sensor, rather than a plurality of mass sensors in a grid. In this example, the grid array is used only in the calculation of the mass footprint or impression of the item in contact with the shelf to create a footprint for the item. The mass of the item is determined by subtracting a previous mass for the entire shelf, including all items on the shelf, from a current mass for the entire shelf, also including all items on the shelf.

Thus, mass change is identified by placing an item on the given shelf and measuring the resultant change in total mass of the shelf. The control application correlates the change in mass with the resultant change in mass footprint data. The change in mass footprint data is due to the additional mass of the item added to the given mass sensor shelf. The change in mass is associated with a newly detected mass footprint for the item. The newly detected mass footprint and the change in mass for the entire shelf are associated with the item placed on the given mass sensor shelf when the change in mass and mass footprint data are detected.

Figure 8:
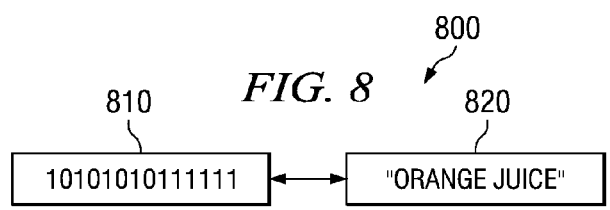
FIG. 8 is a block diagram illustrating an association of an identification code from an identifier tag with a consumable item description in accordance with an illustrative embodiment.

FIG. 8 is a block diagram illustrating an association of an identification code from an identifier tag with a consumable item description in accordance with an illustrative embodiment. Data structure 800 is an example of data stored in a database, such as local database 235 in FIG. 2 and remote database 140 in FIG. 1. The description pair includes a machine readable identification code, such as "10101010111111" associated with identification tag 810. The pair also includes a human readable item description 820 that is associated with identification code "10101010111111" associated with identification tag 810. Other examples of identification codes include, for example, "1234564", "A", or any other code that is unique among all identification codes that a tag reader can read.

In this illustrative example, identification tag 810 having code "10101010111111" is associated with item description "orange juice" 820. An item description is a human understandable description of an item. Human understandable descriptions are for example, text, audio, graphic, or other representations suited for display or audible output.

A user interface and tag reader operates cooperatively with identification tags to identify items for placement in a storage unit and/or identify already placed inside a storage unit. Identification tags, such as identification tag 810 can be any type of identification tag, including Universal Product Code (UPC) bar code identification tags and radio frequency identification (RFID) tags. Radio frequency identification tags include read-only identification tags and read-write identification tags.

A read-only identification tag is a tag that generates a signal in response to receiving an interrogate signal from an item identifier. A read-only identification tag does not have a memory.

A read-write identification tag is a tag that responds to write signals by writing data to a memory within the identification tag. A read-write tag can respond to interrogate signals by sending a stream of data encoded on a radio frequency carrier. The stream of data can be large enough to carry multiple identification codes.

FIG. 9 is a block diagram illustrating an interaction of a user interface and tag reader with an identification tag in accordance with an illustrative embodiment. Control unit 900 is a control unit such as control unit 200 in FIG. 2. Control unit 900 includes a user interface and item identifier(s). Control unit 900 activates an item identifier associated with a storage unit to generate an interrogate signal 910 to form an interrogation zone. Item 920 is located within the interrogation zone of the item identifier. Identification tag 930 associated with item 920 receives interrogate signal 910. In response to receiving interrogate signal 910, identification tag 930 generates response signal 940 via an antenna on the identification tag.

Control unit 900 receives response signal 940. Control unit 900 analyzes response signal 940 to identify an identification code for item 920. Control unit 900 identifies item 920 by identifying an item description, such as item description 820 in FIG. 8, in identifier database 950 associated with the identifier code for identification tag 930.

FIG. 10 is a block diagram illustrating meal plans in accordance with an illustrative embodiment. A set of meal plans includes named ingredients and nutritional information for the meal. A control application compares the nutritional requirements of a given nutritional policy in a set of policies with the nutritional information for each meal plan in the set of meal plans. Each meal plan conforming to a given nutritional policy is placed in a result set for that policy. The control application continues this comparison process until a result set of conforming meal plans has been generated for each nutritional policy corresponding to a set of users. For example, result sets can be generated in accordance with the following exemplary algorithm involving three different nutritional policies:

Result Set 1=SELECT MealPlanName from MealPlanDatabaseTable where PolicyRequirementsofUser1 EQUAL NutritionofMealPlan Result Set 2=SELECT MealPlanName from MealPlanDatabaseTable where PolicyRequirementsofUser2 EQUAL NutritionofMealPlan Result Set 3=SELECT MealPlanName from MealPlanDatabaseTable where PolicyRequirementsofUser3 EQUAL NutritionofMealPlan The control application then generates a list of meal plans common to every result set for every nutritional policy in the set of nutritional policies. The meal plans that are common to all the result sets are identified to form a set of potential meal plans. For example, potential meal plans can be identified in accordance with the following exemplary algorithm:

SELECT MealRecipes from MealsDatabaseTable where MealName is the same between Resultset 1, 2, and 3.

In this manner, a set of potential meal plans conforming to the nutritional requirements of multiple nutritional policies can be generated.

In another embodiment, two or more sets of nutritional polices can be grouped together to form two or more sets of potential meals. For example, if a husband is on a high protein diet, his wife is on a low carbohydrate diet, one child is on a diet free of peanut oil due to allergies, and another child is on a diabetic diet, the nutritional policies for the husband and wife can be combined to generate a set of potential meal plans and the policies for the two children can be combined to form a second set of potential meal plans for the children.

FIG. 11 is a flowchart illustrating a process for selecting a meal plan based on a set of policies in accordance with an illustrative embodiment. The process is implemented by control application 220 in FIG. 2.

The process receives a request for meal plans for a set of individuals (step 1110). The process retrieves a nutritional policy for each individual in the set of individuals to form a set of policies (step 1120). The process determines the nutritional requirements for each policy in the set of policies (step 1130).

The process then queries a meal plan database for a set of potential meals (step 1140) by comparing the nutritional requirement of each policy to the nutritional content of each meal plan. The process determines if a selection for a meal plan to be prepared only from ingredients in a current inventory has been selected by a user (step 1150). If a selection for a meal plan to be prepared from current inventory is selected, the process identifies a set of suggested meal plans from the set of potential meal plans that are able to be prepared from ingredients in current inventory (step 1160) in the correct measure/quantity of the ingredients. The process displays the set of suggested meal plans (step 1170) with the process terminating thereafter.

Returning now to step 1150, if the process determines that the user has not selected to receive meal plans able to be prepared from existing inventory, the process displays all the meal plans in the set of potential meal plans (step 1180). The process receives a selection of a set of potential meal plans to form a set of selected meal plans (step 1190). The process then displays a list of all needed ingredients and the amounts of those ingredients that are not available in current inventory (step 1195) with the process terminating thereafter.

Today, each member of a family frequently has their own unique diet policy. For example, the husband is an athlete trying to build muscle. Therefore, the husband will be on a high protein diet policy. The wife is on a doctor recommended low cholesterol and/or low sodium diet. The child is a diabetic and must adhere to a low sugar diet policy. In a family with multiple diverse diet policies such as this, meal planning and preparation can become incredibly complex. The illustrative embodiments recognize the need for a system that can generate meal plans that meet the requirements of all the diet/nutritional policies in a family from a list of available inventory.

Therefore, the illustrative embodiments provide a technique for providing optimal menu usage of items within a storage unit, such as a refrigerator, by providing generating meal plans based on a plurality of individual nutritional policies and the items currently stored in the storage unit. In this manner, a single meal can be planned rather than preparing multiple different meals to conform to the different diet requirements of different individuals. The illustrative embodiments also simplify shopping for a family having complex diet/nutritional requirements and/or restrictions by providing a method for generating a list of needed ingredients to prepare a given meal plan.

The process receives a request for meal plans for a set of users. The process determines nutritional requirements specified by the set of nutritional policies. The set of nutritional policies correspond to the set of users.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The illustrative embodiments can take the form of an entirely hardware embodiment, an entirely software embodiment or an embodiment containing both hardware and software elements. The illustrative embodiments are implemented in software, which includes but is not limited to firmware, resident software, microcode, etc.

Furthermore, the illustrative embodiments can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the illustrative embodiments have been presented for purposes of illustration and description, and is not intended to be exhaustive or limited to the illustrative embodiments in the form disclosed. Many modifications and variations will be apparent to those of ordinary skill in the art. The embodiment was chosen and described in order to best explain the principles of the illustrative embodiments, the practical application, and to enable others of ordinary skill in the art to understand the illustrative embodiments for various embodiments with various modifications as are suited to the particular use contemplated.

What is claimed is:

1. A method for generating meal plans, the method comprising the steps of:
  responsive to receiving a request for a set of meal plans for a plurality of users, determining, by a processing unit, nutritional requirements specified by a set of nutritional policies, wherein a nutritional policy in the set of nutritional policies specifies the nutritional requirements for a user in the plurality of users;
  identifying, by a processing unit, a plurality of potential meal plans in response to determining the nutritional requirements specified by the set of nutritional policies, wherein each potential meal plan in the plurality of potential meal plans satisfies all nutritional requirements for each user in the plurality of users;
  responsive to receiving a selection of a potential meal plan to form a selected meal plan, determining, by a processing unit, a listing of ingredients required by the selected meal plan;
  for each ingredient in the listing of ingredients:
    determining, by a processing unit and utilizing an item identifier, a quantity of the ingredient in a set of storage units by subtracting a known empty mass of a container of the ingredient from a mass of an item, wherein the mass of the item includes the mass of the ingredient, and wherein the ingredient is one of a plurality of ingredients located on a mass sensor shelf in the set of storage units, and wherein the mass of the ingredient is determined by receiving mass sensor data from a plurality of mass sensors in the mass sensor shelf and associating the mass sensor data from a portion of the plurality of mass sensors with the container of the ingredient based on a surface of the container that is resting on the mass sensor shelf;

locating, by a processing unit, the container of the ingredient on the mass sensor shelf by triangulating location data received from two or more item identifier sensors in the set of storage units to form a location of the ingredient on the mass sensor shelf;

receiving, by a processing unit, the mass sensor data for the item at the location of the container of the ingredient on the mass sensor shelf;

determining, by a processing unit, the mass of the item based on the mass sensor data; and generating, by a processing unit, a listing of ingredients required by the selected meal plan that is unavailable in a current inventory in an amount required by the selected meal plan based on the quantity determined for each ingredient in the listing ingredients in the set of storage units.

2. The method of claim 1 further comprising the step of:
responsive to receiving a selection for meal plans to be prepared from the current inventory, displaying, by a processing unit, a set of suggested meal plans from the plurality of potential meal plans, wherein all ingredients required to prepare each suggested meal plan in the set of suggested meal plans are available in the current inventory of the set of storage units.

3. The method of claim 2 further comprising the step of:
receiving, by a processing unit, a selection of a recommended meal plan to form a selected meal plan, wherein a recipe and nutritional information associated with selected meal plan is displayed.

4. The method of claim 1 wherein the current inventory is an inventory of items available in the set of storage units, and wherein each storage unit in the set of storage units is selected from a group consisting of a refrigeration unit, a pantry, a cupboard, a set of shelves, and a cabinet.

5. The method of claim 1 further comprising the step of:
displaying, by a processing unit, the plurality of potential meal plans for selection by a user.

6. The method of claim 1 further comprising the step of:
displaying, by a processing unit, a recipe and nutritional information associated with the selected meal plan.

7. The method of claim 1 further comprising the step of:
ordering, by a processing unit, all ingredients from the listing of ingredients required by the selected meal plan from a food delivery service provider for delivery to a user.

8. The method of claim 7 wherein the ingredients from the listing of ingredients are ordered in an amount specified by the selected meal plan.

9. The method of claim 1 wherein the plurality of potential meals are identified from a plurality of updateable meal plans.

10. A computer program product for generating meal plans, the computer program product comprising:
a computer readable storage medium;

first instructions to determine nutritional requirements specified by a set of nutritional policies in response to receiving a request for meal plans for a plurality of users, wherein a nutritional policy in the set of nutritional policies specifies the nutritional requirements for a user in the plurality of users;

second instructions to identify a plurality of potential meal plans in response to determining the nutritional requirements specified by the set of nutritional policies, wherein each potential meal plan in the plurality of potential meal plans satisfies all nutritional requirements for each user in the plurality of users;

third instructions to determine, responsive to receiving a selection of a potential meal plan to form a selected meal plan, a listing of ingredients required by the selected meal plan;

fourth instructions to, for each ingredient in the listing of ingredients:
determine, utilizing an item identifier, a quantity of the ingredient in a set of storage units by subtracting a known empty mass of a container of the ingredient from a mass of an item, wherein the mass of the item includes the mass of the ingredient, and wherein the ingredient is one of a plurality of ingredients located on a mass sensor shelf in the set of storage units, and wherein the mass of the ingredient is determined by receiving mass sensor data from a plurality of mass sensors in the mass sensor shelf and associating the mass sensor data from a portion of the plurality of mass sensors with a container of the ingredient based on a surface of the container that is resting on the mass sensor shelf;

locate the container of the ingredient on the mass sensor shelf by triangulating location data received from two or more item identifier sensors in the set of storage units to form a location of the ingredient on the mass sensor shelf;

receive mass sensor data for the item at the location of the container of the ingredient on the mass sensor shelf; and determine the mass of the item based on the mass sensor data; and fifth instructions to generate a listing of ingredients required by the selected meal plan that is unavailable in a current inventory in an amount required by the selected meal plan based on the quantity determined for each ingredient in the listing ingredients in the set of storage units;

wherein the first instructions, the second instructions, the third instructions, the fourth instructions, and the fifth instructions are stored on the computer readable storage medium.

* * * * *